(12) United States Patent
Kalhori et al.

(10) Patent No.: US 10,598,579 B2
(45) Date of Patent: Mar. 24, 2020

(54) CUTTING INSERT FOR CUTTING, MILLING OR DRILLING OF METAL, A TOOL HOLDER AND A TOOL PROVIDED THEREWITH

(71) Applicant: SANDVIK INTELLECTUAL PROPERTY AB, Sandviken (SE)

(72) Inventors: Vahid Kalhori, Gavle (SE); Carl Bjormander, Stockholm (SE); Conny Lundgren, Gavle (SE)

(73) Assignee: SANDVIK INTELLECTUAL PROPERTY AB, Sandviken (SE)

( * ) Notice: Subject to any disclaimer, the term of this patent is extended or adjusted under 35 U.S.C. 154(b) by 0 days.

(21) Appl. No.: 15/735,710

(22) PCT Filed: May 31, 2016

(86) PCT No.: PCT/EP2016/062206
§ 371 (c)(1),
(2) Date: Dec. 12, 2017

(87) PCT Pub. No.: WO2016/202569
PCT Pub. Date: Dec. 22, 2016

(65) Prior Publication Data
US 2018/0180522 A1 Jun. 28, 2018

(30) Foreign Application Priority Data

Jun. 16, 2015 (EP) .................................... 15172403

(51) Int. Cl.
*B23Q 17/09* (2006.01)
*G01N 3/58* (2006.01)
(Continued)

(52) U.S. Cl.
CPC .......... *G01N 3/58* (2013.01); *B23B 27/1614* (2013.01); *B23Q 17/09* (2013.01);
(Continued)

(58) Field of Classification Search
CPC .... G01N 2203/0244; G01N 3/56; G01N 3/58; B23B 2260/128; B23B 2260/144;
(Continued)

(56) References Cited

U.S. PATENT DOCUMENTS 4,744,241 A * 5/1988 Mayer .................... B23Q 17/09
407/113
5,176,053 A 1/1993 Alvelid
(Continued)

FOREIGN PATENT DOCUMENTS

DE 209691 A1 5/1984
DE 3535473 A1 4/1987
(Continued)

*Primary Examiner* — Sara Addisu
(74) *Attorney, Agent, or Firm* — Corinne R. Gorski

(57) ABSTRACT

A cutting insert for cutting, milling or drilling of metal includes a sensor for detecting a predetermined wear of the cutting insert caused by operation thereof on a metal work piece, wherein the sensor includes at least two contact regions through which the sensor is connectable to external measuring circuitry. The sensor has at least two leads, which are connected to a respective of the at least two contact regions, wherein each lead presents a respective free end positioned such that, upon the predetermined wear caused by the operation of the cutting insert on a metal work piece, the free ends will be connected to each other by the metal work piece or by a chip resulting from the operation of the cutting insert on the metal work piece.

15 Claims, 5 Drawing Sheets

(51) Int. Cl.
*B23B 27/16* (2006.01)
*G01N 3/56* (2006.01)
(52) U.S. Cl.
CPC ..... *B23Q 17/0952* (2013.01); *B23Q 17/0995* (2013.01); *G01N 3/56* (2013.01); *B23B 2260/128* (2013.01); *B23B 2260/144* (2013.01); *B23B 2270/48* (2013.01); *G01N 2203/0244* (2013.01)
(58) Field of Classification Search
CPC . B23B 2270/48; B23B 27/1614; B23Q 17/09; B23Q 17/0952; B23Q 17/0995
See application file for complete search history.

(56) References Cited

U.S. PATENT DOCUMENTS

| 6,471,449 | B1 | 10/2002 | Kataoka |
| 2011/0169651 | A1 | 7/2011 | Mitchell et al. |

FOREIGN PATENT DOCUMENTS

| EP | 1095732 | B1 | 9/2006 |
| EP | 1186365 | B1 | 4/2009 |

* cited by examiner

CUTTING INSERT FOR CUTTING, MILLING OR DRILLING OF METAL, A TOOL HOLDER AND A TOOL PROVIDED THEREWITH

RELATED APPLICATION DATA

This application is a § 371 National Stage Application of PCT International Application No. PCT/EP2016/062206 filed May 31, 2016 claiming priority to EP 15172403.6 filed Jun. 16, 2015.

TECHNICAL FIELD

The present invention relates to a cutting insert for cutting, milling or drilling of metal comprising a sensor for detecting a predetermined wear of the cutting insert caused by operation thereof on a metal work piece, wherein the sensor comprises at least two contact regions through which the sensor is connectable to external measuring circuitry.

The invention also relates to a tool for holding a cutting insert according to the invention, as well as a tool comprising a tool holder according to the invention and a cutting insert according to the invention.

BACKGROUND OF THE INVENTION

In machining with exchangeable and/or indexable cutting inserts there is an increased need to measure on-line the changes of condition that the cutting insert is subjected too close to the cutting zone thereof during operation. On basis of such on-line measurement of the condition of the cutting insert, decisions regarding altering of operation parameters, exchange of cutting insert or repositioning of the cutting insert in its holder can be taken. Time-requiring manual inspection of the condition of the cutting insert can be avoided and, as a consequence thereof, an improved efficiency and a more automated operation can be obtained. Furthermore, a precise on-line measurement of the condition of the cutting insert, and correct measures taken in the right time as a consequence thereof, will help to prevent damaging of the work piece due to use of excessively worn cutting inserts or too high temperatures.

Prior art as disclosed in EP1186365B1 and EP 1095732B1 describes cutting inserts in which a sensor for on-line measurement of the wear of the cutting insert comprises an electric circuit formed by a conductive layer provided on the cutting insert, and wherein the electric circuit comprises at least two contact regions through which the electric circuit is connectable to external measuring circuitry. A cutting insert holder presents corresponding electrical contacts which are electrically connected to a respective of the contact regions of the cutting inserts as the cutting insert is held in an operative position by the tool holder. Connected to the contacts of the tool holder there is provided measuring circuitry for measuring of a change of resistance of the electric circuit caused by a predetermined wear of the cutting insert. The measuring circuitry comprises means for generating an electric current in the electric circuit provided on the cutting insert during operation thereof. A lead, or sensor line, of the electric circuit is positioned on a clearance face of the cutting insert in close proximity to a cutting edge of the cutting insert and extends along the cutting edge. The lead of the electric circuit is positioned such that, upon a predetermined wear of the cutting edge, the lead will be in engagement with the work piece, and the resistance of the electric circuit as measured by means of said external measuring circuitry will change. At a predetermined critical degree of wear of the cutting insert, the lead will be cut, indicating that the cutting insert must be exchanged or be given another position in the holder. On basis of the wear down of the lead and finally the cutting off thereof, it is thus detected how far the wear of the cutting insert has proceeded, and, depending thereon, measures such as exchange of the cutting insert may be taken.

However, with the suggested solution as disclosed by EP1186365B1 and EP 1095732B1, the signal obtained in the external circuitry, indicating that the wear down of the cutting insert has proceeded to a certain point, may not always be so stable due to fluctuating engagement between the work piece and the lead of the electric circuit of the cutting insert.

U.S. Pat. No. 4,744,241 discloses a method and an arrangement for detecting a wear limit or a break in a cutting edge of a machine tool. At least two conductor paths are embedded in the cutting material forming the cutting edge, one of the conductor paths being part of a closed circuit and the other of the conductor paths being part of an open circuit. A signal serving to break off the machining process is produced if either the conductor path of the closed circuit is interrupted or the conductor path of the open circuit is closed by the creation of a conductive connection between the two conductor paths. The conductor path of the closed circuit is arranged along the cutting edge of the cutting insert so as to be interrupted by a crack propagating in a region of a secondary cutting edge of the latter, as a result of a predetermined wear of the cutting insert. However, in cutting processes, a conductive bridge may be formed across a crack by particles of the material of the work piece or the coolant or by particles of an electrically conductive cutting substance, so that, in spite of the fact that the limit of permissible wear has been reached or a break in the cutting edge has occurred, the signal for breaking off the machine is not initiated by any signal from the interrupted closed circuit. In order to cope with that drawback U.S. Pat. No. 4,744,241 suggests the provision of the above-mentioned conductor path of an open circuit which is positioned in parallel with and arranged to be electrically connected to the conductor path of the closed circuit upon a predetermined degree of wear of the cutting insert. Upon such interconnection, a signal for breaking off the machining process is assumed to be initiated. However, since the conductor path of the closed circuit is arranged so as to be interrupted by a crack, and might in fact be interrupted by one or more such cracks at the moment when that conductor path is connected to the conductor path of the open circuit, also this signal for breaking off the machining process might not be initiated. The signal received from any of the circuits runs the risk of being non-distinct since the conductor path of the closed circuit may be interrupted by a crack but may be temporarily closed through the above-described formation of a conductive bridge across the crack or cracks. It will thus be unclear whether a predetermined wear of the cutting insert has occurred or not, and the indication of the predetermined wear becomes unreliable.

Moreover, the position of the crack or the wear down of the cutting insert cannot be determined on basis of signals received from the above-mentioned circuits.

It is an object of the present invention to present a cutting insert that enables a more precise and reliable detection of a predetermined wear of a cutting insert caused by operation of the cutting insert on a metal work piece.

SUMMARY OF THE INVENTION

The object of the invention is achieved by means of a cutting insert for cutting, milling or drilling of metal comprising
- a sensor for detecting a predetermined wear of the cutting insert caused by operation thereof on a metal work piece, wherein
- the sensor comprises at least two contact regions through which the sensor is connectable to external measuring circuitry, the cutting insert being characterised in that
- the sensor comprises at least two leads which are connected to a respective of the at least two contact regions, wherein
- each lead presents a respective free end positioned such that, upon the predetermined wear caused by the operation of the cutting insert on a metal work piece, the free ends will be connected to each other by the metal work piece or by a chip resulting from the operation of the cutting insert on the metal work piece.

The provision of a sensor defining an open circuit having at least two leads with a respective free end, wherein the free ends are positioned so as to be electrically interconnected by the metal work piece or the chip when predetermined conditions are fulfilled, enables positioning of the leads such that the risk of any of these leads being interrupted by a crack propagating from the region of the cutting edge of the cutting insert is very small. A closed circuit without a free end, on the other hand, will always have a part thereof which runs generally in parallel to the cutting edge, and will therefore be more susceptible to interruption by a propagating crack, thereby making such measurement unreliable.

According to one embodiment, the sensor is used for sensing wear of one of the edges of a cutting insert. In a zone of the cutting insert in which wear in form of cracks are likely to propagate from the cutting edge the free ends of the leads extend with an angle to, possibly even generally perpendicularly to the cutting edge the wear of which is measured by means of the sensor. In other words, in said zone or region the leads are non-parallel with the cutting edge for which the sensor is arranged to measure wear. In said zone or region the leads may extend straight or in a curved fashion. If they extend with a curvature, the tangent of each point of the curve will intersect the cutting edge with an angle. The free ends of the leads may extend such that they intersect the cutting edge or they may end at a predetermined distance from the cutting edge.

The free ends are positioned with such a distance between each other and to the cutting edge that they are directly contacted by the metal work piece or the chip and electrically interconnected thereby. Based on the exact knowledge of the position of the free ends it can be determined with great precision where on the cutting insert a predetermined wear has occurred. The free ends of the leads may be covered by a protective layer provided on top thereof or be exposed. They may be provided at such depth under such a protective layer that they are contacted by the metal work piece or a chip only upon a predetermined wear down of a layer that covers the leads. If they are not covered by a protective layer, i.e. exposed on the surface of the cutting insert, they should end at such a distance from the cutting edge that they are contacted by the metal work piece or chip only upon a predetermined wear of the cutting insert.

The leads may be provided as a thin layer on a substrate or underlying layer of the cutting insert or be provided in any other suitable form, such as a wire or the like. In this context, layer is not limited to layers covering a substantial part of a surface, but includes also layers in the form of narrow stripes, strings or small regions provided on a surface, which may cover only a minor part thereof.

According to one embodiment, the free ends of the leads are positioned such that the tips thereof will be contacted by and interconnected by the metal work piece or a chip thereof when the predetermined wear occurs. The leads may extend in the direction of expected progression of wear on the cutting insert from the cutting edge for which wear is measured by means of the sensor. The leads are thus positioned such that, as the metal work piece or the chip continues to wear down the cutting insert it also continuously shortens the length of the leads in a direction from the tip of free ends thereof, and thereby gradually reduces the electric resistance of the circuit as the wear down progresses. The change of electric resistance of the circuit including the leads can be registered by the above-mentioned external measuring circuitry and be used as a measured indication of the progress of the wear down of the cutting insert. In other words, not only recognition of the immediate occurrence of a predetermined wear down is enabled with the suggested provision of leads, their free ends and tips, but also the further progression of such wear down.

The external measuring circuitry can be arranged to register two defined situations, for example a first situation wherein the free ends of the at least two leads are disconnected and a second situation wherein the free ends are connected (by a work piece or a chip). This can be done by sending an electric current through one of the leads and measuring if the current flows through the associated other lead. As discussed above, it is also possible to measure the electrical resistance in the leads.

According to one embodiment where the free ends are arranged to be interconnected by a chip, two adjacent associated leads are arranged at a distance from each other which is less than the smallest expected chip width. Thereby it is achieved that the sensor of the cutting insert will function also when the cutting insert is operated with small cutting depth.

According to one such embodiment, the cutting insert has two adjacent cutting edges which are connected by a nose edge which defines a segment of a circle having a radius r, and, at least in an area in which the free ends of the leads will be connected to each other by the metal work piece or by a chip resulting from the operation of the cutting insert on the metal work piece in case the predetermined wear occurs, the distance between adjacent free ends of said at least two leads is less than the radius r, also defined as the nose radius. One of the cutting edges is the cutting edge associated to the sensor, and towards which the free ends of the leads are directed for the purpose of being interconnected by a chip or a metal work piece as this cutting edge is used during operation of the cutting insert and wear on the cutting insert is caused as a result thereof. The leads are arranged at a distance from each other which is approximately the nose radius. These two leads should extend towards the cutting edge very close to the nose, and preferably with a maximum distance from the nose corresponding to the nose radius. This is advantageous because cutting inserts usually are operated with cutting equal to or depths larger than the nose radius. It is thus ensured that the width of cut chips will be larger than the distance between the two leads during all normal operations.

According to one embodiment, the distance between adjacent free ends of said at least two leads in said area is less than 1 mm. Thereby, also when the cutting insert is operated with very small cutting depth, it is ensured that a chip would be sufficiently wide to interconnect the leads.

According to one embodiment, at least in the region of the free ends of the sensor, the sensor is covered by a protective layer forming an electric insulation thereon. Thereby, the risk of having unintentional interconnection of the leads or having fluctuating signals indicating changes of the electric resistance of the closed circuit caused by, for example, unintentional fluctuating motion of chip or generation of a bridge between said lead by the coolant or by particles of an electrically conductive cutting substance may be avoided.

According to one embodiment, in a region extending from a tip of the free end of at least one of the leads and a predetermined distance along the lead towards the contact region connected to that lead, the lead presents a higher resistance per length unit than in the remaining parts of the lead. As wear caused by the metal work piece or the chip progresses, the free end of the lead is also worn down. As, during operation of the cutting insert, the free end of the lead is worn down by the metal work piece or the chip, the resistance of the circuit is reduced. This difference in electric resistance is measured by means of the external measuring circuitry. Thus, a certain change in resistance will correspond to a certain reduced length (wear) of the leads, which in turn corresponds to a certain wear of the cutting insert. Since the resistance of the leads in a region extending from a tip of the free end towards the contact region presents a higher resistance per length unit than the remaining parts of the lead, the change of electric resistance becomes relatively large for a predetermined wear progression. Accordingly, a more clear indication of the wear progression is obtained. It is possible to arrange each or some of the free ends with such a section of higher resistance.

Advantageously, the lead or leads have a distance with such higher resistance per length unit that corresponds to the length of the area of suspected wear. The distance can correspond to the length of acceptable wear.

According to one embodiment, in the region presenting a higher resistance per length unit than the remaining parts of the lead, the lead has a reduced cross section.

According to one embodiment, the cutting insert is, in the region of the lead presenting a higher resistance per length unit than the remaining parts of the lead, the lead has a reduced width. In embodiments where the leads are provided as a conductive layer, the leads may have the reduced width in the plane of the conducting layer forming the lead. Such reduction of the cross-section of the lead can be accomplished by means of laser cutting of the layer, either before application of a protective and electrically insulating layer on top of the leads or after such application.

According to one embodiment, the sensor comprises more than two contact regions and more than two leads, each lead being connected to a respective associated contact region, wherein the free end of one of the leads is positioned so as to be connected to any of at least two other leads by a metal work piece or a chip thereof depending on which predetermined wear that is obtained as a result of the operation of the cutting insert on the metal work piece. On basis of the knowledge of the position of the respective free ends, and on basis of which free ends that are contacted and interconnected by the metal work piece or a chip thereof, a more precise picture of the progressing wear down of the cutting insert may be obtained. An external measuring circuitry should be arranged so as to register which free ends are interconnected, and the machining operation should be controlled with regard thereto.

According to one embodiment, there is provided a solid electric insulator between the leads. Thereby, the risk of having an unintended electric short cut between the leads is reduced compared to the alternative design in which there is open space between the leads. A solid electric insulator may also be a better insulator than air, which will alternatively be the medium occupying an open space between the leads.

According to one embodiment wherein at least in the region of the free ends of the sensor, the sensor is covered by a protective layer forming an electric insulation, the solid insulator is a part of the protective layer. In such a case, the leads can be formed by means of a laser cutting operation applied onto an electrically conducting layer provided on a substrate of the cutting insert and the protective layer is subsequently applied onto the conducting layer, i.e. onto the leads, thereby also filling the gap, or open space, generated between the leads as a result of the laser cutting operation. Typically the protective layer is applied by means of a deposition process such as physical vapour deposition, PVD, or chemical vapour deposition, CVD.

According to one embodiment, the protective layer essentially consists of alumina. Alumina has the advantage of being a material often chosen as an outer layer of a cutting insert because of its physical properties. Its high electrical resistivity also contributes to the choice thereof as a solid insulator between the leads.

According to one embodiment, the free ends of the leads are located on a rake face of the cutting insert in an area susceptible to be subjected to crater wear caused by chips removed from a metal work piece during operation of the cutting insert on the metal work piece. According to one such embodiment, the free ends of the at least two leads 9-14 are located in an area between the associated cutting edge and a chip breaker.

According to one embodiment, the free ends of the leads are located not more than 0.3 mm from a cutting edge defined by an intersection between the rake face and a clearance face of the cutting insert. This is advantageous because in normal operation this corresponds to area where chips are formed and thus in constant contact with cutting insert. In a corresponding area at clearance surface, the work piece may come into contact with the cutting insert as the edge wears down.

According to one embodiment, in the area susceptible to be subjected to crater wear, the leads extend with an angle in a direction towards to the associated cutting edge of which corresponding crater wear is to be measured. In said area, the leads extend with an angle in the range of 45°-135, or 65°-105°, or 85°-95° relative said cutting edge. If the leads are curved, the tangent of each point along said curve will intersect the cutting edge with an angle within the above-defined ranges. Thus, the leads extend in a direction of expected wear propagation and the risk of a crack that propagates from the cutting edge cutting a lead is small.

According to one embodiment, in the area susceptible to be subjected to crater wear, the free ends of the leads extend generally with the same distance to each other, for example in parallel with each other.

According to one embodiment, the contact regions are located on a clearance face of the cutting insert, wherein said clearance face is a face that intersects the rake face. In particular for an indexable cutting insert, which comprises a sensor according to the invention for each active cutting edge thereof, such a design is favourable. Each sensor may have its set of contact regions disposed on a separate clearance face such that, for each operative position of the cutting insert in a holder, the contact regions of the sensor associated to the cutting edge to be used is connected to corresponding contacts in the holder.

According to one embodiment, the cutting insert comprises a rake face and at least one clearance face intersecting the rake face, wherein the free ends of the leads are located on the clearance face in an area close to a cutting edge of the cutting insert, in which area the cutting insert it susceptible to be subjected to wear caused by a metal work piece during operation of the cutting insert on the metal work piece. According to one embodiment, in the area in which the cutting insert it susceptible to be subjected to wear caused by the metal work piece, the leads extend with an angle to the most adjacent cutting edge of the cutting insert in a direction towards said cutting edge. In said area, the leads extend with an angle in the range of 45°-135, or 65°-105°, or 85°-95° relative said cutting edge. The free ends of the leads may also extend in parallel with each other in said area. According to yet another embodiment, the free ends of the leads are located not more than 0.3 mm from the most adjacent cutting edge defined by an intersection between the rake face and a clearance face of the cutting insert.

According to one aspect, the invention relates to a tool holder for holding a cutting insert as defined hereinabove or hereinafter, the tool holder being characterised in that it presents electrical contacts which are electrically connected to a respective of the contact regions of the cutting inserts as the cutting insert is held in an operative position by the tool holder.

According to another aspect, the invention relates to a tool for the cutting, milling or drilling of metal, comprising a tool holder as defined hereinabove or hereinafter and a cutting insert as defined hereinabove or hereinafter, the tool being characterised in that it comprises measuring circuitry for measuring of a change of resistance of the electric circuit caused by the predetermined wear of the cutting insert, the measuring circuitry being connected to the sensor of the cutting insert through the contacts of the tool holder.

Further features and advantages of the present invention will be presented in the following detailed description of embodiments of the invention, with reference to the annexed drawing.

BRIEF DESCRIPTION OF THE DRAWINGS

Embodiments of the invention will now be presented with reference to the annexed drawing, on which.

DETAILED DESCRIPTION OF THE INVENTION

Figure 1:
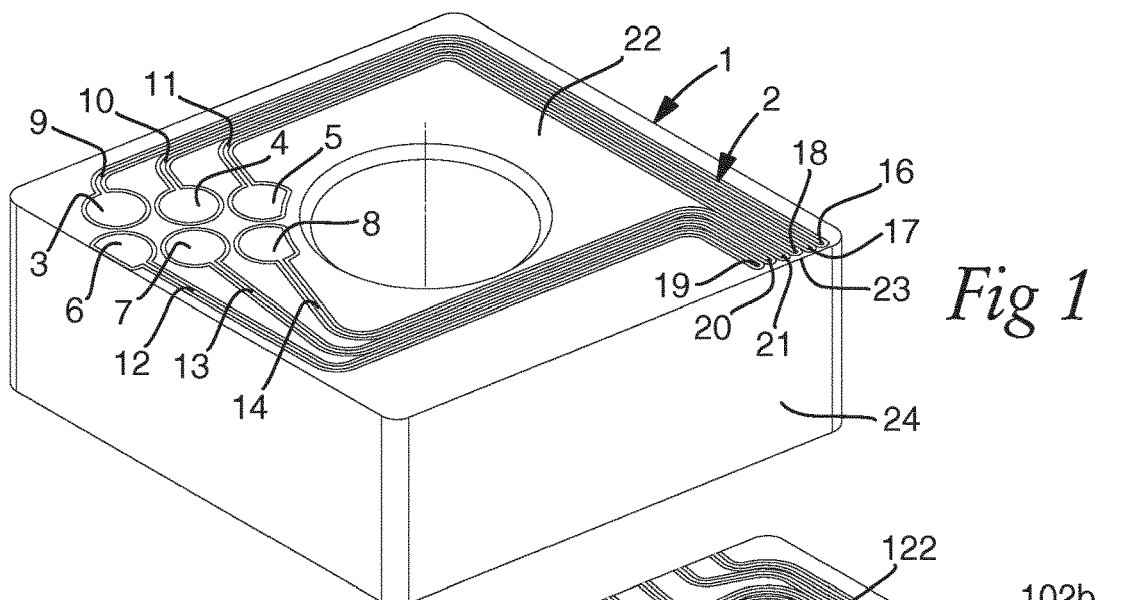
FIG. 1 is a perspective view of a first embodiment of a cutting insert according to the invention.

FIG. 1 shows a cutting insert 1 for cutting of metal. The cutting insert 1 comprises a sensor 2 for detecting a predetermined wear of the cutting insert 1 caused by operation thereof on a metal work piece, wherein the sensor 2 comprises an open electric circuit formed by parts of an electrically conductive layer forming part of the cutting insert 1. Though not shown in FIG. 1, the cutting insert is provided with a protecting and electrically insulating layer on top of the electrically conductive layer. However, in order to facilitate the disclosure of the sensor design, the protecting layer is not shown in the figure.

The sensor 2 comprises a number of contact regions 3-8 through which leads 9-14 of the electric circuit is connectable to external measuring circuitry (indicated with reference number 15 in FIGS. 6 and 7). The contact regions 3-8 are exposed and not covered by any protective layer and are thus easily connectable to corresponding contacts of an external measuring circuitry. The contact regions 3-8 and the leads 9-14 have been generated by removal of surrounding portions of the electrically conducting layer, typically by means of laser cutting, such that a pattern like the one shown in FIG. 1 is obtained.

The electric circuit is an open circuit, wherein the respective leads 9-14 are interconnected with a respective of the contact regions 3-8. Each lead 9-14 presents a respective free end 16-21 positioned such that, upon the predetermined wear caused by the operation of the cutting insert 1 on a metal work piece, the free ends 16-21 of at least some of the leads 9-14 will be electrically interconnected to each other by the metal work piece or by a chip resulting from the operation of the cutting insert 1 on the metal work piece.

In the embodiment shown in FIG. 1, the free ends 16-21 of the leads 9-14 are located on a rake face 22 of the cutting insert 1 and are directed towards a cutting edge 23 of the cutting insert 1. The cutting edge 23 is defined by an intersection between the rake face 22 and a clearance face 24 of the cutting insert 1. The free ends 16-21 are located in an area susceptible to be subjected to crater wear caused by chips removed from a metal work piece during operation of the cutting insert 1 on a metal work piece. The free ends 16-21 of the leads 9-14 are located not more than 0.3 mm from the cutting edge 23, typically in an area between a chip breaker (not shown) on the rake face and the cutting edge 23. The maximum distance between adjacent free ends 16-21 in this area is less than the width of a chip to be formed. Therefore, the maximum distance between adjacent free ends 16-21 in said area is less than the nose radius of a nose edge connecting the cutting edge with an adjacent cutting edge. Typically, the distance between adjacent free ends 16-21 in said area is less than 1 mm. Thus, upon operation of the cutting insert 1 by means of the most adjacent cutting edge 23 towards which said free ends 16-21 are directed, at least some of these free ends 16-21 will be interconnected by a chip from a work piece that is worked on by the cutting insert 1 upon a predetermined wear of the cutting insert 1 caused by a chip removed from the work piece. Provided that the leads 9-14 are connected to an external measuring circuitry as shown in FIG. 7, and that there is an electric potential difference between the leads, electrical interconnection may be used as an indication of the predetermined wear on the cutting insert 1, and further measures, such as exchange of the cutting insert, may be taken on basis thereof.

Figure 4:
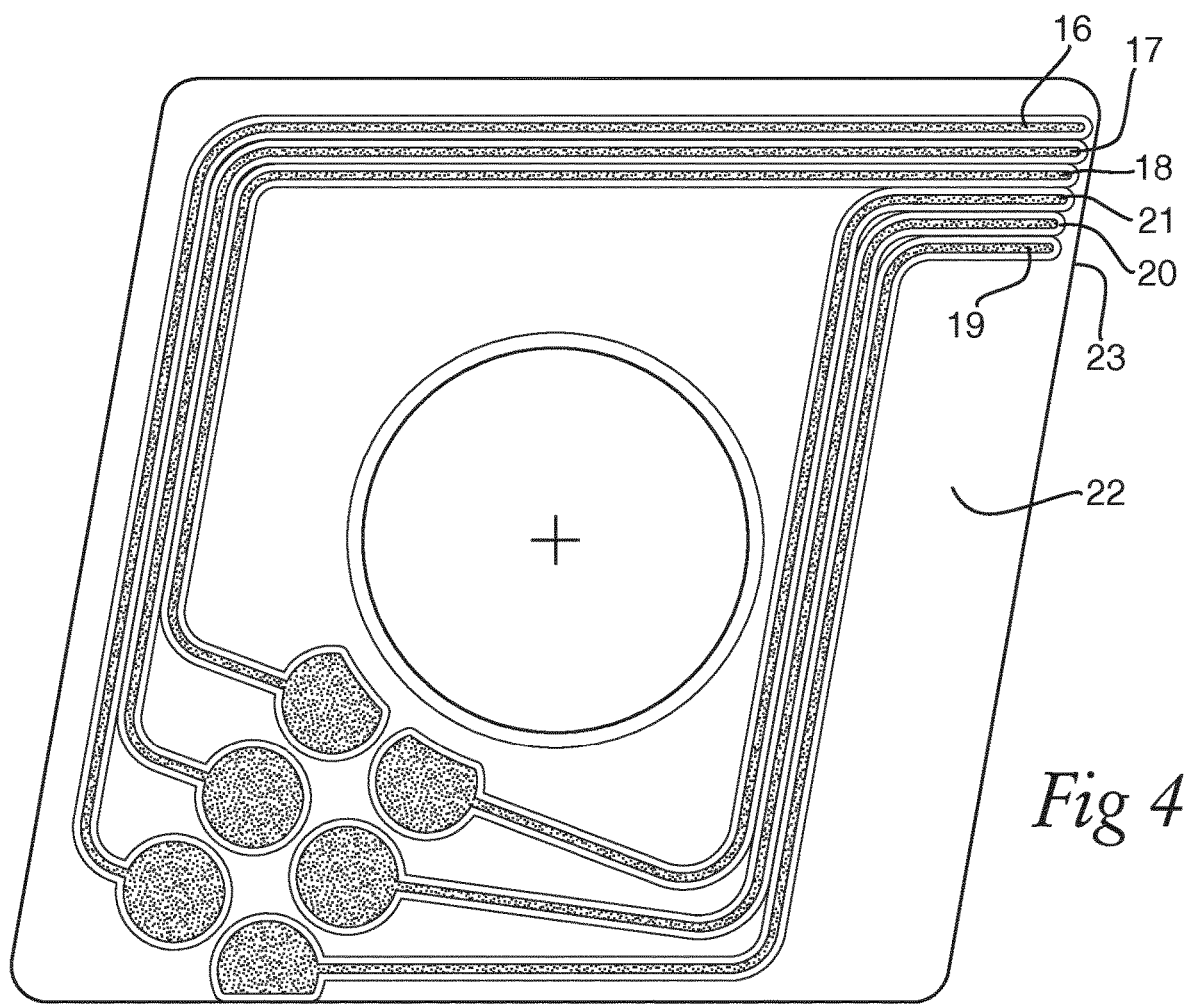
FIG. 4 is an enlarged view of a rake face of the cutting insert shown in FIG. 1.

As can be seen in FIG. 4, the free ends 16-21 of the leads 9-14 are generally parallel in an end region thereof. In said end region, they are directed with an angle to the most adjacent cutting edge 23 towards which they are directed.

Figure 5:
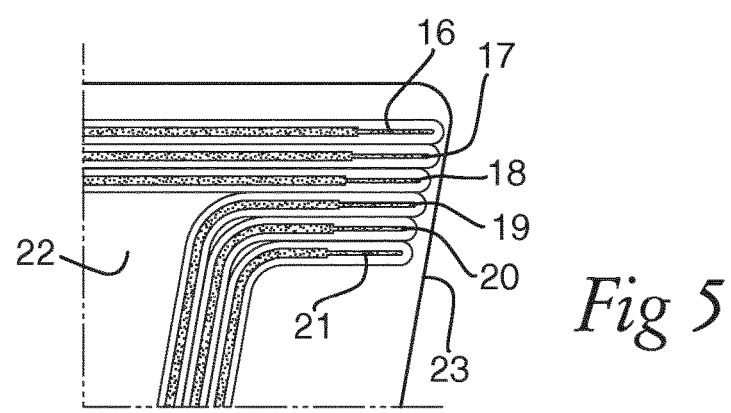
FIG. 5 is an enlarged view of a portion of the rake face shown in FIG. 5, FIGS. 6a and 6b are perspective views from different angles showing a first embodiment of a tool according to the invention equipped with a tool holder according to the invention and a cutting insert according to the invention.

FIG. 5 shows the end region of the free ends 16-21 in further enlargement. In a region extending from a tip of each of the free ends 16-21 and a predetermined distance along each of the leads 9-14 towards each of the contact regions 3-8, the lead presents a higher electric resistance per length unit than in the remaining parts of the lead. In the region presenting a higher resistance per length unit than the remaining parts of the lead, the respective lead 9-14 has a reduced cross section. In the region of the lead 9-14 presenting a higher electric resistance per length unit than the remaining parts of the lead, the lead 9-14 has a reduced width in the plane of the conducting layer forming the lead 9-14, resulting in the above-mentioned higher electric resistance. As, during operation, wear of the cutting insert continues and electrically interconnected free ends 16-21 in the above-mentioned region are worn down, the change in electric resistance of the sensor 2 will be relatively larger than if no provision of higher electric resistance per length unit of the respective free end 9-14 of the leads 9-14 would have been provided. In the region presenting a higher resistance per length unit than the remaining parts of the lead, the respective lead 9-14 has a width of 5 μm-60 μm. In said remaining parts, the width of the lead is 100 μm-1 mm, preferably 100 μm-300 μm. If there is no region presenting a higher resistance per length unit than the remaining parts of the lead, the lead width is in the range of 10 μm-1 mm, preferably 30 μm-300 μm The free end 16-21 of each lead 9-14 may be electrically interconnected to more than one other free end 16-21 of the leads 9-14. This means that that the sensor 2 comprises more than two contact regions 3-8 and more than two leads 9-14, each lead being connected to a respective associated contact region 3-8, wherein the free end 16-21 of one of the leads 9-14 is positioned so as to be connected to any of at least two other leads 9-14 by a metal work piece or a chip thereof depending on which predetermined wear that is obtained as a result of the operation of the cutting insert 1 on the metal work piece. Thus, by means of an external measuring circuitry, it is determined which leads that are electrically interconnected and thus the character of the wear. In the embodiments shown in FIG. 1-3 the tips of the free ends 16-21 of the leads 9-14 are at the same distance from the most adjacent cutting edge 23. Embodiments in which there are more than two leads 9-14 and the tips of the free ends 16-21 of the leads 9-14 are positioned at different distances from the cutting edge 23 are also envisaged, thereby enabling further possibilities of detecting the degree of wear down of the cutting insert 1.

Figure 2:
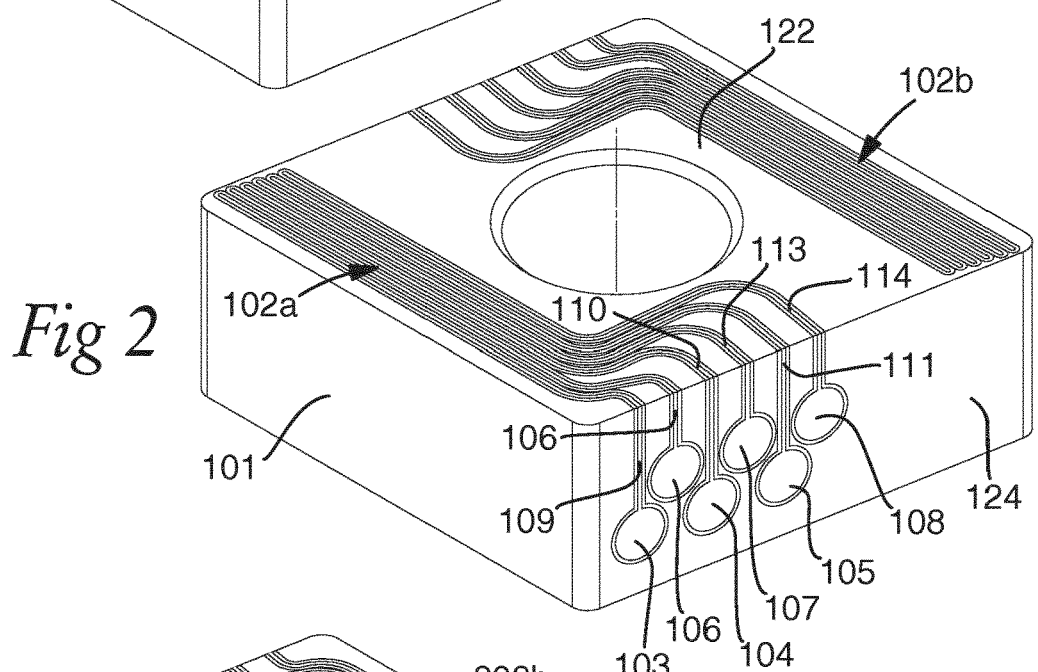
FIG. 2 is a perspective view of a second embodiment of a cutting insert according to the invention.

FIG. 2 shows an alternative embodiment which differs from the one shown in FIG. 1 in that the contact regions 103-108 of the cutting insert 101 are located on a clearance face 124, and that the leads 109-114 thus extend differently from the free ends thereof to the contact regions 103-108 compared to the embodiment shown in FIG. 1. In the embodiment shown in FIG. 1, the contact regions 3-8 are located on the rake face 22. The embodiment shown in FIG. 2 also differs from that shown in FIG. 1 in that it presents two sensors 102*a* and 102*b* on one and the same side of the cutting insert 101, in this case the rake face 122.

Figure 3:
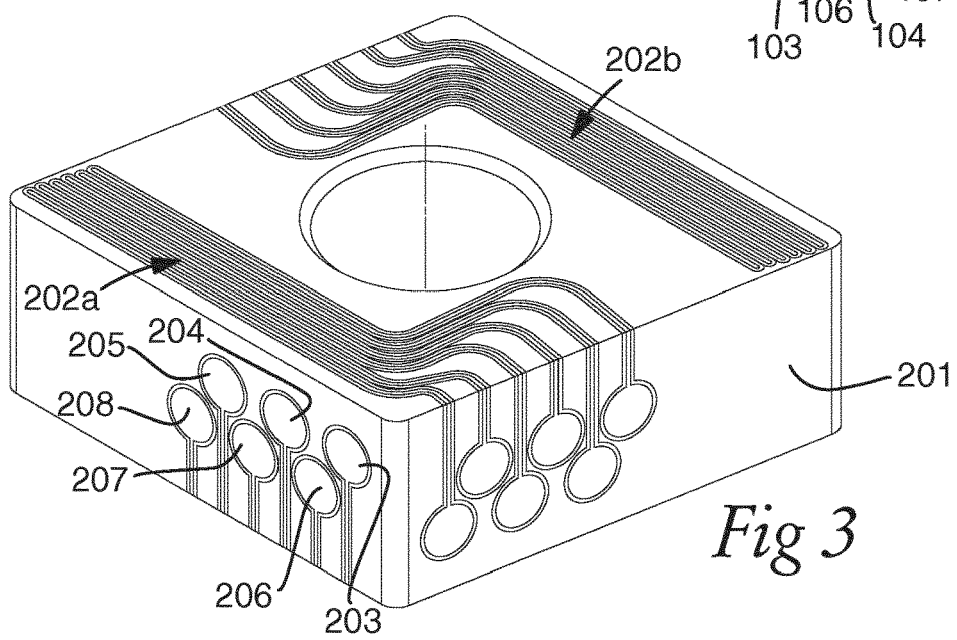
FIG. 3 is a perspective view of a third embodiment of a cutting insert according to the invention.

FIG. 3 shows yet another embodiment which differs from the embodiment shown in FIG. 2 in that it has corresponding sensors on opposite rake faces of a cutting insert that is indexable by turning upside down. The contact regions 203-208 of one of two sensors on the opposite rake face is shown in FIG. 3.

It should be understood that the present invention also envisages embodiments in which the sensors are provided on one or more of the clearance faces and in which the contact regions of the sensors are either positioned on the clearance faces or on the rake faces. Such embodiments are not shown on figures here but as to the design and functionality of the leads, especially the free ends thereof, they follow the principles disclosed hereinabove for the embodiments in which the sensors are provided on the rake faces. The difference is that the free ends of the leads are positioned in an area which is assumed to be subjected to wear caused by the work piece rather than by a chip removed therefrom. In said area, the free ends of the leads are directed towards the most adjacent cutting edge, the wear of which is to be indicated by the sensor. In said area, the free ends may be generally parallel to each other and extend with an angle to said cutting edge. Embodiments in which sensors are provided both on the rake faces an on the clearance faces and which, thus, enables simultaneous detection of wear caused by the work piece and the chip are also envisaged.

Figure 6A:
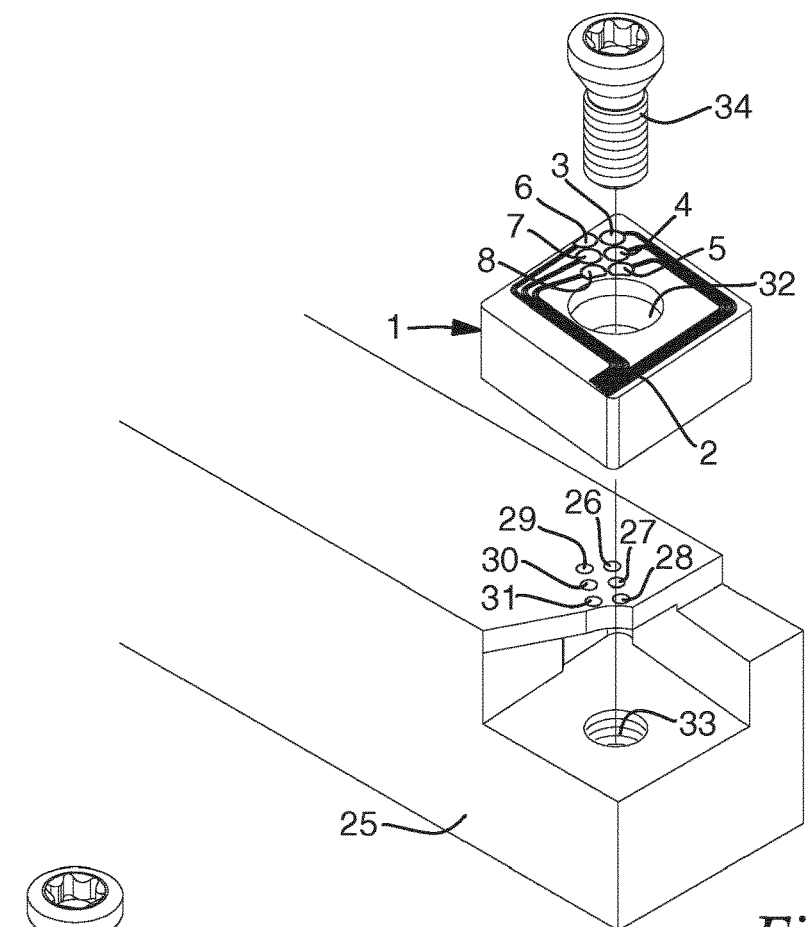
Figure 6B:
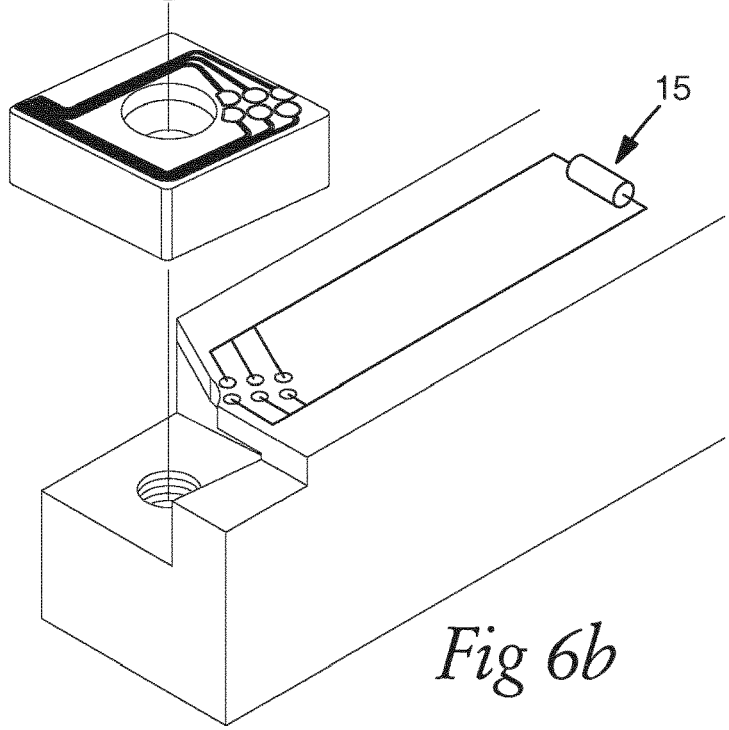

FIGS. 6*a* and 6*b* show a tool for the cutting of metal, comprising a tool holder 25 aimed for holding a cutting insert 1 according to the embodiment shown in FIG. 1. The tool comprises measuring circuitry 15 (only indicated in FIG. 6*b* for reasons of clarity) connected to the tool holder 25 for measuring of a change of resistance of the electric circuit as defined hereinabove caused by a predetermined wear of the cutting insert 1. The tool holder 25 has electrical contacts 26-31 which are to be electrically connected to a respective of the contact regions 3-8 of the cutting insert 1 as the cutting insert 1 is held by the tool holder 25. Here the electrical contacts 26-31 are exposed on a lower side of a projection provided on the holder, such that they will be in contact with the contact regions of the cutting insert once the latter has been attached on the holder. The measuring circuitry 15 is connected to the electric circuit, i.e. the sensor 2, of the cutting insert 1 through the contacts 26-31 of the tool holder 25. The cutting insert 1 has a through hole 32 in the rake face 22 and there is provided a screw hole 33 in the holder 25, enabling fastening of the cutting insert 1 to the holder 25 by means of a screw 34.

Figure 7A:
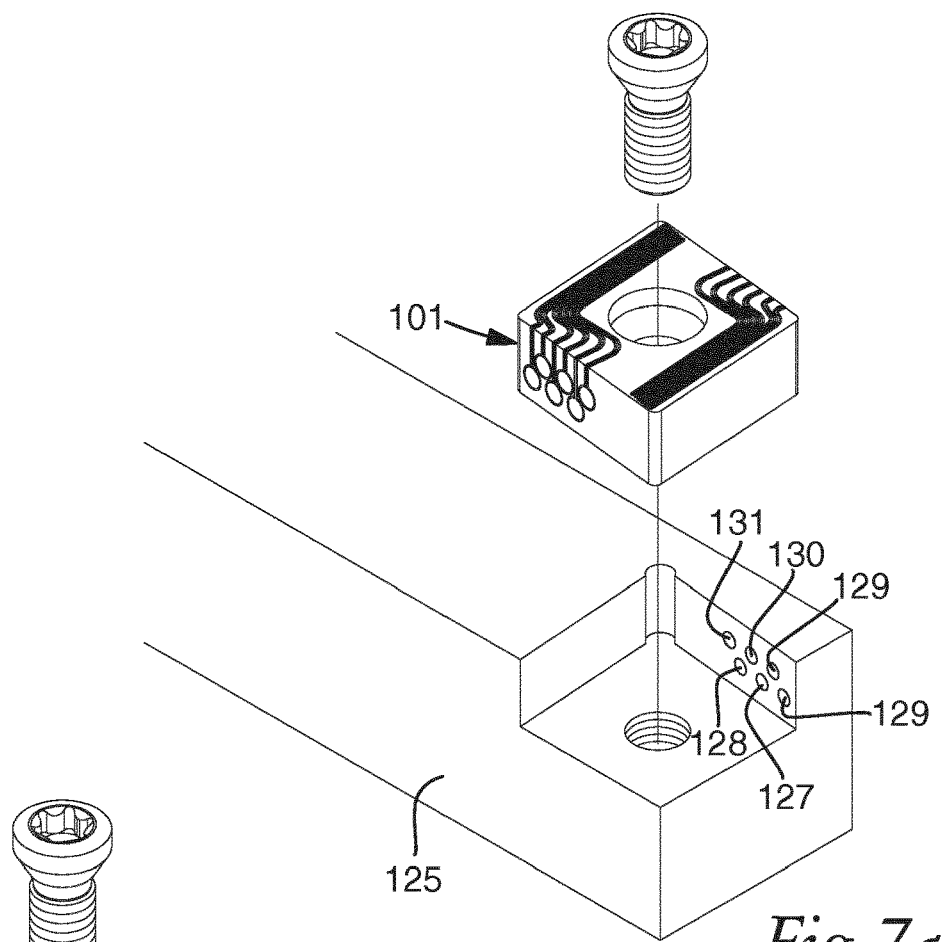
FIGS. 7a and 7b are perspective views from different angles showing a second embodiment of a tool according to the invention equipped with a tool holder according to the invention and a cutting insert according to the invention.
Figure 7B:
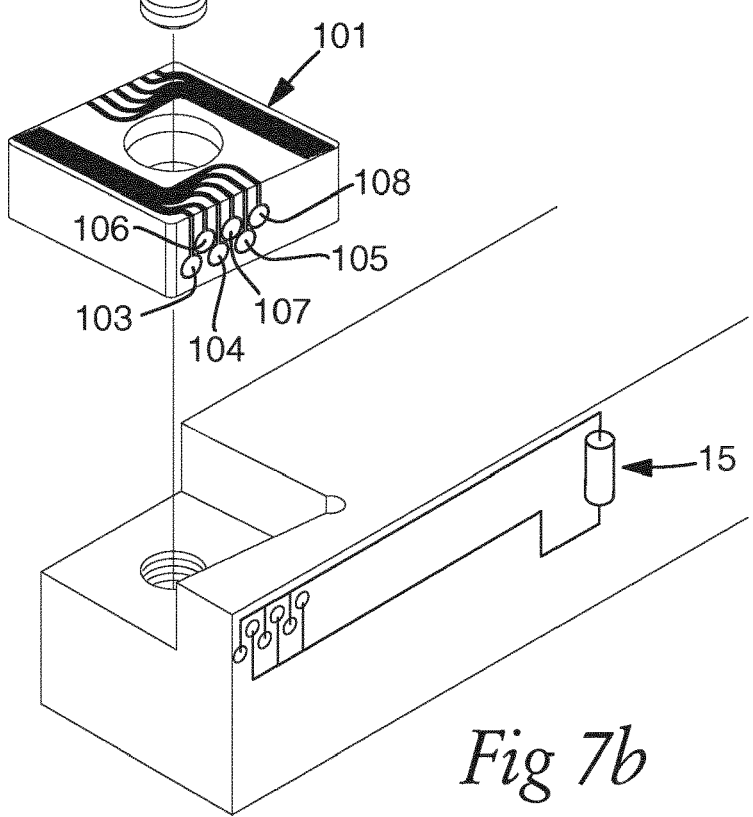

FIGS. 7*a* and 7*b* show a tool for the cutting of metal, comprising a tool holder 125 aimed for holding a cutting insert 101, 201, according to the embodiments shown in FIGS. 2 and 3. In this exemplifying embodiment, the tool comprises a cutting insert 101 according to the embodiment disclosed with reference to FIG. 2. The tool holder 125 has electrical contacts 126-131 which are to be electrically connected to a respective of the contact regions 103-108 of the cutting insert 1 as the cutting insert 101 is held by the tool holder 125. The contacts 126-131 are provided on a support surface on the tool holder 125 against which a clearance face of the cutting insert 101 bears when the cutting insert 101 is attached to the holder 125.

Alternatively, with a different positioning of the contact regions on the clearance face 124 of the cutting insert 101, the contacts on the tool holder 125 could be provided on another support surface on the tool holder 125 against which another clearance surface of the cutting insert 101 bears.

FIGS. 8*a*-8 and 9*a*-9*b* show first and second embodiments of coating designs of a cutting insert according to the invention. Before describing the specific embodiments shown in FIGS. 8a-8c and 9a-9b the general principles of the coating design will be discussed.

A cutting insert according to the present invention has a substrate, for example cemented carbide, typically tungsten carbide with a cobalt binder, on which at least one electrically conducting layer is applied, which will form the sensor or sensors of the invention. The electrically conducting layer may be applied only on areas that will define the contact regions and the leads of the sensors, or it may be applied to a more widespread area whereupon the contact regions and leads are cut or etched out of that conducing layer. The conducting layer is not necessarily directly applied onto the substrate. There may be one or more other layers provided between the electrically conducting layer and the substrate. However, the layer nearest below the electrically conducting layer should be electrically insulating. If the substrate is electrically insulating, the electrically conducting layer could thus be applied directly onto the substrate. On top of the electrically conducting layer, or at least on top of the parts thereof that define or will define free ends of leads of the sensor, there may be provided an electrically insulating protective layer, for example an alumina layer. There may be further electrically conducting layers provided in the coating, as long as they are electrically insulated from the electrically insulating layer that will define said sensor.

A sensor could be formed by a contact region and its associated lead that are defined by one electrically conducting layer and a contact region and its associated lead that are defined by another electrically conducting layer in a coating comprising more than one electrically conducting layer. Likewise, different sensors could be defined by different conducting layers provided at different levels in a set of layers forming a coating on the substrate.

Contact regions and leads of a sensor may be cut out by means of laser from an electrically conducting layer before application of a protective layer thereon, or after application of a protective layer thereon. If cutting out of the contact regions and leads is performed before application of the protective layer, the protective layer may, and should be applied such that it also occupies spaces formed around said contact regions and leads, thereby electrically insulating the latter further from surrounding parts of the conducting layer and/or from adjacent contact regions or leads. Contact regions covered by the protective layer must be exposed by subsequent removal of the protective layer covering them.

Figure 8A:
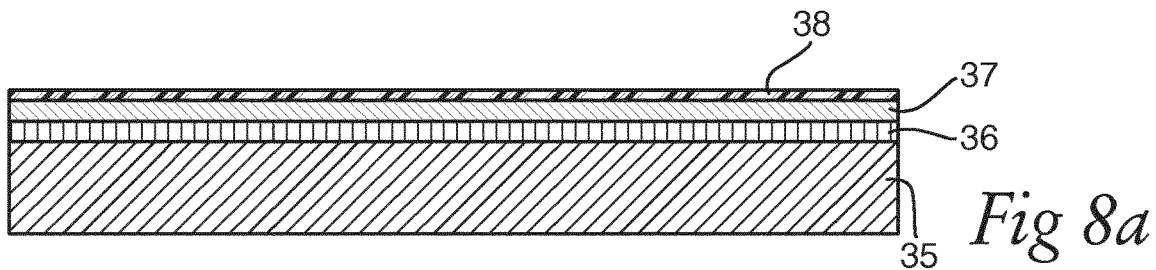
FIGS. 8a, 8b and 8c are cross sections of part of a cutting insert according to the invention, according to one embodiment.
Figure 8B:
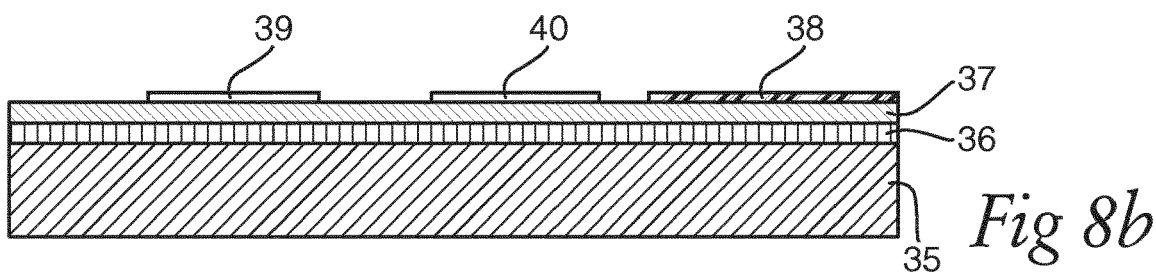
Figure 8C:
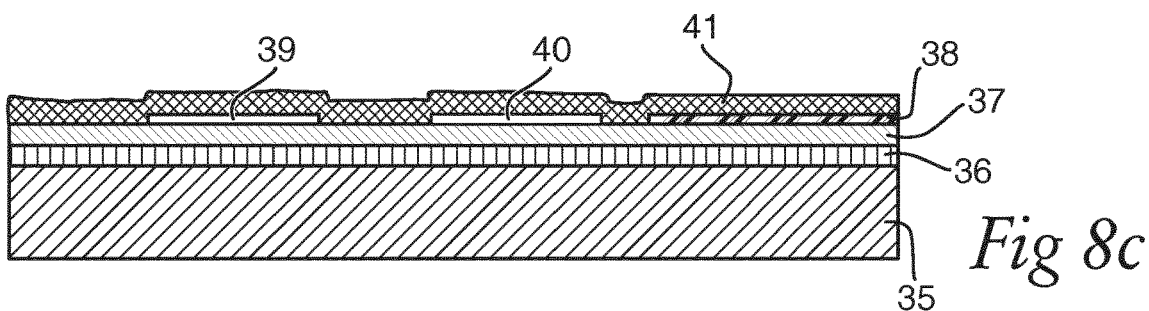

Now, reference is made to FIG. 8a-8c. The presented coating design could be used for any of the embodiments of the cutting inserts 1, 101, 201 disclosed hereinabove. A substrate of the cutting insert 1, 101, 201 is denoted 35. The substrate 35 may comprise any material suitable for the purpose, such as cemented carbide, typically tungsten carbide with a cobalt binder.

It is suggested that the sensor or sensors of the cutting inserts 1, 101, 201 are based on the general coating design obtained by deposition of a functional wear resistant CVD coating that is applied onto the substrate and forms part of the cutting insert. Accordingly, on the substrate 35 there is provided an inner layer 36, typically comprising Ti(C, N, O). Other compositions are also envisaged, such as those based on Zr(C, N) or Hf(C, N). The thickness of the inner layer is in the range of 1 μm-15 μm.

On top of the inner layer 36 there is provided a thermal barrier layer 37, typically α-$Al_2O_3$, possibly κ-$Al_2O_3$. It is suggested to apply the thermal barrier layer 37 by means of chemical vapor deposition. The thickness of the thermal barrier layer 37 is in the range of 1 μm-15 μm.

On top of the thermal barrier layer 37, there is provided an electrically conducting layer 38, typically comprising a suitable nitride and/or carbide such as TiN and/or TiC. It is suggested to apply the electrically conducting layer 38 by means of chemical vapor deposition. The thickness of the electrically conducting layer 38 is in the range of 0.1 μm-5 μm.

Before application of an electrically insulating protective layer 41 on top of the electrically conducting layer 38, laser is used for cutting out leads 39, 40 and contact regions (not visible in FIG. 8) from the conducting layer 38 (FIG. 8b).

After cutting out of the leads 39, 40 and the associated contact regions of the sensor or sensors, the electrically insulating protective layer 41 is applied such that it covers at least essential parts of the sensors, in particular the free ends thereof aimed to be interconnected by a metal work piece or a chip during operation of the cutting insert. It is suggested to apply the protective layer 41 by means of chemical vapor deposition, CVD, whereby the protective layer 41 totally covers the underlying electrically conducting layer 38, including the leads and contact regions of the sensor or sensors. The protective layer 41 also fills spaces between the leads, contact regions and surrounding parts of the electrically conducting layer, which spaces were generated as a result of the cutting out of the leads and the contact regions from the electrically conducting layer. The protective layer 41 typically comprises κ-$Al_2O_3$, possibly α-$Al_2O_3$ and has a thickness in the range of 0.5 μm-10 μm. Other electrically insulating and protective layers are off course also envisaged. For example, the protective layer 41 may comprise $ZrO_2$.

Figure 9A:
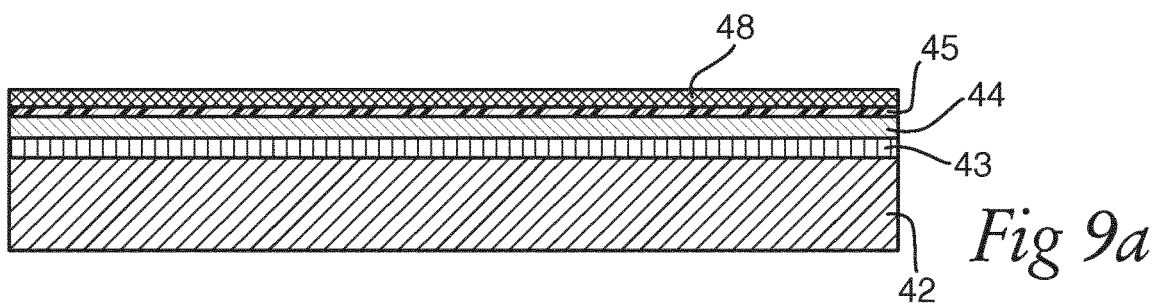
FIGS. 9a and 9b are cross sections of a part of a cutting insert according to the invention, according to another embodiment.
Figure 9B:
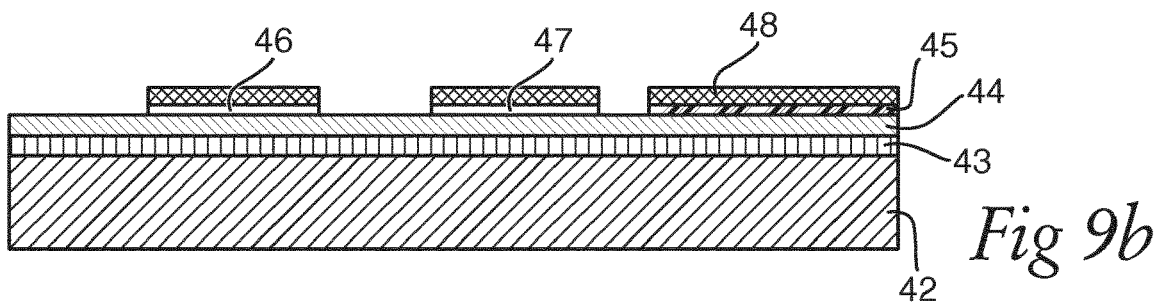

FIGS. 9a and 9b show an alternative embodiment of a coating design and a method of generating such a design. The cutting insert, which could be any of the cutting inserts 1, 101, 201 disclosed hereinabove with reference to FIGS. 1-3, comprises a substrate 42 onto which there is applied an inner layer 43 corresponding to the inner layer 36 disclosed with reference to FIG. 8a-8b.

On the inner layer 43 there is provided a thermal barrier layer 44 corresponding to the thermal barrier layer 37 disclosed with reference to FIGS. 8a-8b.

On the thermal barrier layer 44 there is provided an electrically conducting layer 45 corresponding to the electrically conducting layer disclosed with reference to FIGS. 8a-8b.

On the electrically conducting layer 45, but before cutting out the leads and contact regions of the sensor or sensors, there is provided a protective layer 48 which corresponds to the protective layer 38 disclosed with reference to FIGS. 8a-8c. After application of the protective layer 48, leads 46, 47 and contact regions (not visible in FIGS. 9a and 9b) are cut out of the electrically conducting layer 45 by means of laser cutting. Thereby, open spaces will remain between leads, contact regions and surrounding electrically conducting layer 48.

The invention claimed is:

1. A cutting insert for cutting, milling or drilling of metal comprising a sensor arranged to detect a predetermined wear of the cutting insert caused by operation thereof on a metal work piece, the sensor including at least two contact regions through which the sensor is connectable to external measuring circuitry, the sensor defining an open circuit having at least two leads, which are connected to a respective of the at least two contact regions, wherein each lead presents a respective free end, the free ends being spaced by a distance therebetween and from a cutting edge of the insert such that, upon the predetermined wear caused by the operation of the cutting insert on the metal work piece, the free ends of the leads become directly electrically interconnected to each other by the metal work piece or by a chip resulting from the operation of the cutting insert on the metal work piece.

2. The cutting insert according to claim 1, further comprising two adjacent cutting edges which are connected by a nose edge which defines a segment of a circle having a radius, and that, at least in an area in which the free ends of the leads will be connected to each other by the metal work piece or by a chip resulting from the operation of the cutting insert on the metal work piece, the distance between adjacent free ends is less than said radius.

3. The cutting insert according to claim 1, wherein at least in the region of the free ends of the sensor, the sensor is covered by a protective layer forming an electric insulation thereon.

4. The cutting insert according to claim 1, wherein in a region extending from a tip of the free end of at least one of the leads and a predetermined distance along the lead towards the contact region connected to the lead, the lead presents a higher resistance per length unit than in remaining parts of the lead.

5. The cutting insert according to claim 4, wherein in the region presenting a higher resistance per length unit than the remaining parts of the lead, the lead has a reduced cross section.

6. The cutting insert according to claim 1, wherein the sensor includes more than two of the contact regions and more than two of the, each lead being connected to a respective associated contact region, wherein the free end of one of the leads is positioned so as to be connected to any of at least two other leads by a metal work piece or a chip thereof depending on which predetermined wear that is obtained as a result of the operation of the cutting insert on the metal work piece.

7. The cutting insert according to claim 1, wherein between the leads there is provided a solid electric insulator.

8. The cutting insert according to claim 1, wherein the free ends of the leads are located on a rake face of the cutting insert in an area susceptible to be subjected to crater wear caused by chips removed from a metal work piece during operation of the cutting insert on the metal work piece.

9. The cutting insert according to claim 8, wherein the free ends of the leads are located at most 0.3 mm from a cutting edge defined by an intersection between the rake face and a clearance face of the cutting insert.

10. The cutting insert according to claim 8, wherein in the area susceptible to being subjected to crater wear, the free ends of the leads extend with an angle to an adjacent cutting edge of the cutting insert, for which cutting edge wear is measured by the sensor.

11. The cutting insert according to claim 1, wherein in the area susceptible to being subjected to crater wear, the free ends of the leads extend generally in parallel.

12. The cutting insert according to claim 1, wherein the contact regions are located on a clearance face of the cutting insert intersecting the rake face.

13. The cutting insert according to claim 1, further comprising a rake face and at least one clearance face intersecting the rake face, and that the free ends of the leads are located on the clearance face in an area close to a cutting edge of the cutting insert, in which area the cutting insert it susceptible to be subjected to wear caused by a metal work piece during operation of the cutting insert on the metal work piece.

14. The cutting insert according to claim 13, wherein the free ends of the leads are located not more than 0.3 mm from a cutting edge defined by an intersection between the rake face and a clearance face of the cutting insert.

15. A tool for the cutting, milling or drilling of metal, comprising a cutting insert according to claim 1, wherein the tool holder presents electrical contacts, which are electrically connected to a respective of the contact regions of the cutting insert as the cutting insert is held in an operative position by the tool holder, and a measuring circuitry for measuring of a change of resistance of the sensor caused by the predetermined wear of the cutting insert, the measuring circuitry being connected to the sensor of the cutting insert through the contacts of the tool holder.

* * * * *